(12) United States Patent
Costovici

(10) Patent No.: US 9,095,669 B2
(45) Date of Patent: Aug. 4, 2015

(54) SYSTEM FOR HEATED GAS INSUFFLATION IN PATIENTS

(76) Inventor: Nicolas Anthony Costovici, Roses-Gerona (ES)

( * ) Notice: Subject to any disclaimer, the term of this patent is extended or adjusted under 35 U.S.C. 154(b) by 47 days.

(21) Appl. No.: 14/006,480

(22) PCT Filed: Mar. 27, 2012

(86) PCT No.: PCT/ES2012/000074
§ 371 (c)(1),
(2), (4) Date: Sep. 20, 2013

(87) PCT Pub. No.: WO2012/131120
PCT Pub. Date: Oct. 4, 2012

(65) Prior Publication Data
US 2014/0012187 A1    Jan. 9, 2014

(30) Foreign Application Priority Data

Mar. 31, 2011    (ES) .................................. 201130500

(51) Int. Cl.
*A61M 13/00*    (2006.01)
*A61M 16/10*    (2006.01)

(52) U.S. Cl.
CPC ............ *A61M 13/003* (2013.01); *A61M 13/006* (2014.02); *A61M 16/1075* (2013.01); *A61M 2205/3368* (2013.01)

(58) Field of Classification Search
CPC .......... A61M 16/1045; A61M 16/105; A61M 16/106; A61M 16/1065; A61M 16/107; A61M 16/1075; A61M 13/00; A61M 13/003; A61M 13/006

USPC ........... 128/204.17; 600/560; 604/23, 24, 25, 604/26, 113, 114

See application file for complete search history.

(56) References Cited

U.S. PATENT DOCUMENTS

| | | |
|---|---|---|
| 3,856,051 A | 12/1974 | Bain |
| 5,006,109 A | 4/1991 | Douglas et al. |
| 5,400,778 A * | 3/1995 | Jonson et al. ............ 128/205.19 |
| 5,411,474 A | 5/1995 | Ott et al. |
| 6,041,777 A * | 3/2000 | Faithfull et al. .......... 128/200.24 |
| 6,131,571 A * | 10/2000 | Lampotang et al. ..... 128/204.21 |

(Continued)

FOREIGN PATENT DOCUMENTS

| | | |
|---|---|---|
| EP | 1192968 | 4/2002 |
| WO | WO9927988 | 6/1999 |
| WO | WO03092776 | 11/2003 |

OTHER PUBLICATIONS

Translation International Preliminary Report PCT/ES2012/000074.

*Primary Examiner* — Nicholas Lucchesi
*Assistant Examiner* — Anh Bui
(74) *Attorney, Agent, or Firm* — Notaro, Michalos & Zaccaria P.C.

(57) ABSTRACT

A system includes an insufflator provided with a gas inlet, a valve that regulates the flow to be supplied, an adjustable heater for the gas to be supplied, a sensor that detects the temperature of the heated gas, an outlet for supplying the gas, and a mechanism for propelling the gas toward the supply outlet. A disposable supply duct can be coupled to the gas outlet for the insufflator in order to convey the heated gas into the patient and a return duct for the gas is connected to a distal area of the supply duct and to an inlet of the heater, wherein the gas supply duct and the gas return duct form a continuous recirculation circuit for heated gas.

9 Claims, 2 Drawing Sheets

(56) References Cited

U.S. PATENT DOCUMENTS

| | | | |
|---|---|---|---|
| 7,591,267 B2 * | 9/2009 | Mashak et al. | 128/205.28 |
| 7,814,908 B2 * | 10/2010 | Psaros | 128/205.28 |
| 7,870,857 B2 * | 1/2011 | Dhuper et al. | 128/203.25 |
| 2004/0045549 A1 | 3/2004 | Smith et al. | |
| 2007/0157929 A1 * | 7/2007 | Radomski et al. | 128/204.18 |
| 2009/0107982 A1 * | 4/2009 | McGhin et al. | 219/497 |

* cited by examiner

SYSTEM FOR HEATED GAS INSUFFLATION IN PATIENTS

OBJECT OF THE INVENTION

The present invention relates to a system for heated gas insufflation in patients, of the type comprising:—an insufflator provided with: a gas inlet, a valve that regulates the gas flow to be supplied, an adjustable heater for the gas to be supplied, a sensor that detects the temperature of the heated gas and an outlet for supplying the gas; and—a disposable supply duct that can be coupled to the gas outlet of the insufflator in order to convey the gas supplied and heated by the insufflator into a patient's cavity.

FIELD OF APPLICATION

This invention is applicable in the medical field, to introduce a heated gas into a patient's cavity during different testing and surgical procedures such as colonoscopy, laparoscopy, hysteroscopy, or any others.

BACKGROUND OF THE INVENTION

In conducting certain medical tests and surgical procedures, it is usual to insufflate a gas, usually $CO_2$, in a patient's cavity.

Gas heating for medical insufflators is very important. For certain invasive surgery, such as laparoscopy, hysteroscopy, or others, heating of the gas is important to prevent fog on camera lenses and dropping of the patient's temperature during the procedure.

For other procedures such as virtual colonoscopy, it is also convenient to supply hot gas because it relaxes the patient's muscles, enhances distension and reduces the risk of spasms Currently there are insufflator systems that incorporate heating means for the gas to be supplied to the patient.

The trouble with high flow insufflators (applicable in procedures such as laparoscopy or hysteroscopy) is the significant variation in flow and room temperature. The gas flow supplied must be continuously regulated to maintain pressure as constant as possible in the insufflated cavity. This flow may vary from 0 to 50 liters/minute during the test or procedure to be performed.

Currently insufflators, having a gas inlet, a valve that regulates the flow of gas to be supplied, and an outlet for supplying the gas, to which a disposable duct that conveys the insufflator supplied gas into a patient's cavity is coupled, are well known. These insufflators are also currently used in combination with a gas heater.

In some cases, the gas heater is arranged inside the insufflator, heating the gas before it leaves the insufflator.

The problem with this technology is that an exact temperature cannot be reached inside the patient. Due to the fact that the duct arranged between the machine and the patient is of a certain length and that the temperature of the room is usually from 12° C. to 25° C., there is a great loss of calories during the transit of gas through the duct, between the patient and the insufflator. This loss of calories depends on the room temperature and the flow. If the flow is stopped or is very low, then the gas available in the duct is cooled and when the flow circulates again, the cool gas contained in the duct is automatically pushed into the patient. It is also very difficult to calculate the heat setting when the flow frequently changes from 0 to 50 liters/minute.

Heating systems, in which the heater is arranged outside the insufflator, are also well known, specifically at an area near the end of the duct that is intended to be introduced into a patient's cavity.

This solution has the advantage of preventing the loss of calories in the gas available in the duct, between the machine and the patient, but this heating system is very difficult to regulate in order to obtain a constant temperature at the output of the duct. This system requires regulation of the heater on the basis of the variable gas flow supplied to the patient and use of a heater with low reaction time that may be stopped or heated when the gas flow changes. Therefore it is necessary to accurately adapt the heating to the gas flow introduced into the patient. These constraints cause that this heating system typically has a very low precision.

The technical problem, which arises in this invention, is the development of a system for heated gas insufflation in patients, which allows for continuous gas supply available at the duct outlet, just before the patient's cavity, at a very precise and constant temperature, irrespective of changes in the flow of gas intended to be introduced into the patient's cavity.

DESCRIPTION OF THE INVENTION

The system for heated gas insufflation in patients of this invention has features that are aimed at achieving heated gas supply and delivery to the patient at a uniform temperature, and to minimize temperature changes produced in known systems due to cooling of heated gas in its passage between the insufflator and the patient, particularly when significant fluctuations of the gas flow to be supplied to the patient are produced during the performance of a test or procedure.

This system is of the type comprising:—an insufflator provided with: a gas inlet, a valve that regulates the flow of gas to be supplied, an adjustable heater for the gas to be supplied, a sensor that detects the temperature of the heated gas, an outlet for supplying the gas and means for propelling the gas toward the supply outlet and;—a disposable supply duct that can be coupled to the gas outlet of the insufflator in order to convey the gas supplied and heated by the insufflator into a patient's cavity.

To solve the above problems and according to the invention, this system comprises a gas return duct connected to the supply duct at an area near the end intended to be introduced into a patient's cavity and into a heater input, the gas supply duct and the gas return duct forming a circuit for continuous circulation of heated gas at a constant supply temperature by means of the heater.

This system allows the supply of gas at a given temperature between 20° C. to 50° C. depending on the application to which it is intended (Laparoscopy, Hysteroscopy, CT colonography, or others).

By arranging a continuous recirculation circuit of the heated gas it is possible to accurately determine calorie loss, due to the temperature of the room, since the gas is supplied to the supply duct and returns to the heater. It is possible to calculate the difference between the intake temperature and the output temperature and to determinate the output temperature required to achieve the desired temperature at the distal end of the supply duct.

The gas temperature does not vary significantly depending on the gas flow required; by providing velocity to the circulating gas, the gas supplied to the patient is not dependent on the gas available in the supply duct as in current systems.

According to the invention, the system comprises a storage reservoir between the heater and the supply duct, through which the gas heated in the insufflator circulates. This storage reservoir provides a heated gas reserve and a very good heating response while avoiding sudden drops in gas temperature in case it is necessary to supply the patient with a high gas flow.

In the invention it is envisaged that the supply duct has a temperature sensor at a distal area, near the end intended to be introduced into the patient's cavity. This temperature sensor measures the heated gas drop between the insufflator and the area near the patient, and facilitates configuration of heater settings, especially in those cases where the patient requires the supply of a high gas flow.

An additional feature of the system of the invention is the provision, at least in the return duct, of filters for cleaning the circulating gas. These filters prevent possible contamination of the insufflator by the circulating gas.

According to the invention the gas recirculation circuit has an exhaust valve through which controlled exhaust of the circulating heated gas is carried out. This relief valve ensures continued gas flow from the insufflator to the supply duct, preventing the return of gas through said supply duct from the patient to the insufflator and possible contamination in the insufflator due to the return of gas through the supply duct.

According to the invention the heated gas recirculation circuit comprises, at least, one mechanical safety valve arranged inside the insufflator, and an electronic safety valve for releasing possible gas overpressure in the recirculation circuit outside.

In various embodiments of the invention said electronic safety valve may be arranged: either inside the insufflator and connected to the gas recirculation circuit at an area located between the return duct and the heater, said electronic safety valve having an outlet to the insufflator outside, or outside the insufflator and connected to the distal area of the gas supply duct, by means of a bypass duct. This external arrangement of the electronic safety valve further reduces the risk of contamination of the insufflator.

DESCRIPTION OF FIGURES

In order to complement the current description and for the purpose of facilitating an understanding of the characteristics of the invention, the present description is accompanied by a set of drawings wherein, by way of a non-limiting example, the following has been represented.

PREFERRED EMBODIMENT OF THE INVENTION

Figure 1:
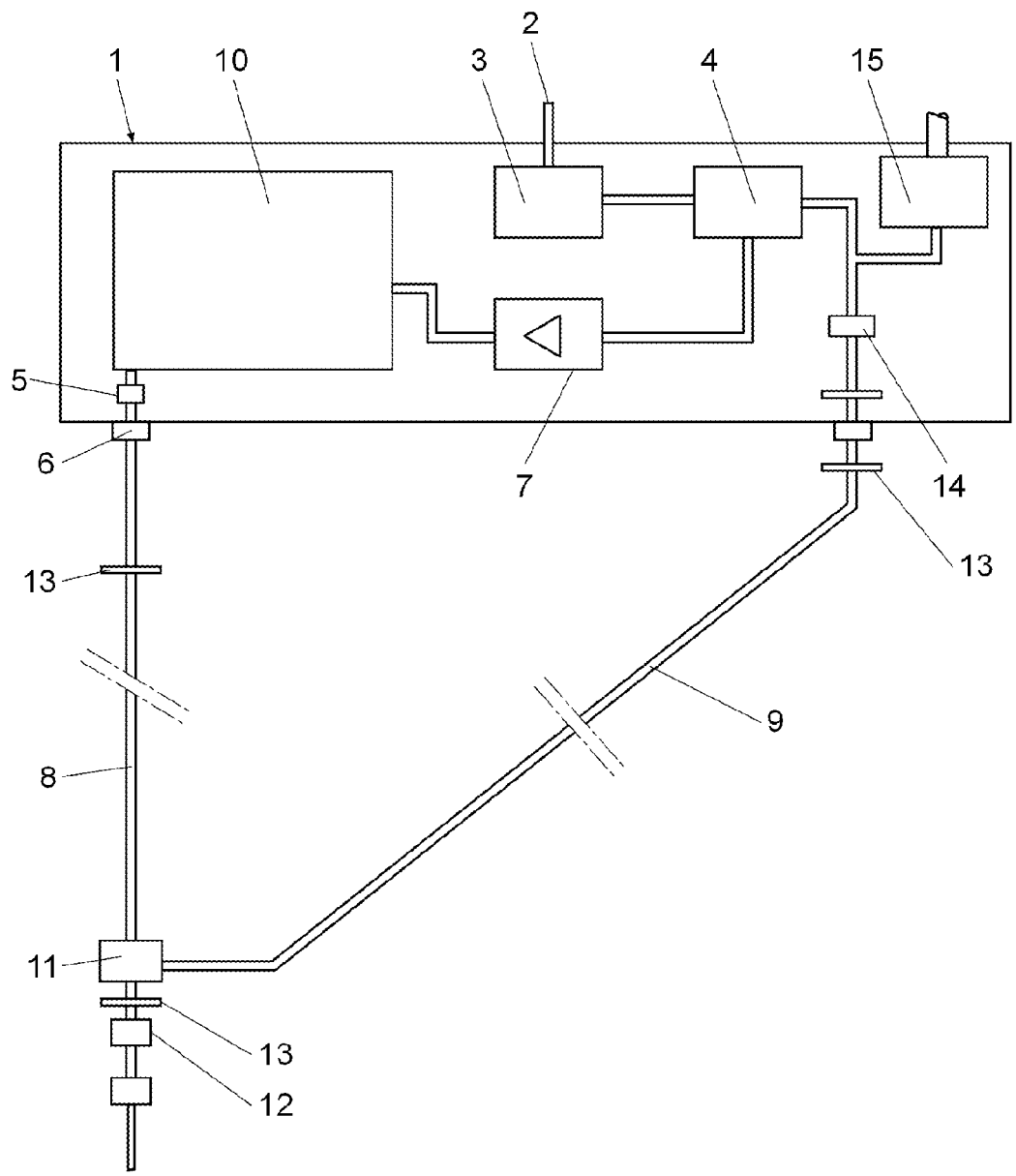
FIG. 1 shows a schematic view of an embodiment example of the system for heated gas insufflation in patients according to the invention, and in which the electronic safety valve against overpressures is arranged inside the insufflator.

In the embodiment shown in the attached figure, the insufflator, referenced in its entirety as (1), has a gas inlet (2), a valve (3) that regulates the flow of gas to be supplied, an adjustable heater (4) for the gas to be supplied, a sensor (5) that detects the temperature of the heated gas, an outlet (6) for supplying the gas, and means (7) for propelling the gas toward the supply outlet (6).

The system further comprises a disposable supply duct (8), that may be coupled to the insufflator outlet (6) in order to convey the gas, heated and supplied by the insufflator (1), into a patient's cavity, and a return duct (9) for the gas, connected to the supply duct (8) in an area near the end intended to be introduced in a patient's cavity and to an inlet of the heater (4).

The gas supply duct (8) and the gas return duct (9) form a continuous circulation circuit for the heated gas at a constant supply temperature, and propelled by the propelling means (7).

In the example shown, the system comprises a storage reservoir (10) situated between the heater (4) and the supply duct (8), and through which the gas heated in the insufflator circulates, said storage reservoir (10) maintaining a heated gas reserve allowing for a supply of 50 liters/minute of gas, without inducing appreciable temperature variation.

At a distal area near the end intended to be introduced into the patient's cavity, the supply duct (8) has a temperature sensor (11), which measures the temperature drop of the gas circulating between the heater (4) and the gas introduction area into the patient, and facilitates adjustment of the heater (4) in order to ensure the introduction of gas into the patient at a stable and determined temperature.

The system comprises an exhaust valve (12) through which controlled exhaust of the circulating gas is adjusted, thus ensuring a continuous flow thereof from the heater (4) toward the return duct (9).

In the example shown, the system comprises, in the supply duct (8) and in the return duct, filters (13) for cleaning the circulating gas and to prevent the contamination of the insufflator (1).

The system comprises, in the gas recirculation circuit, a mechanical safety valve (14), which is arranged inside the insufflator (1).

Additionally the system comprises an electronic safety valve (15) for releasing gas overpressures in the gas recirculation circuit to the outside.

In the example shown in FIG. 1, said electronic safety valve (15) is arranged inside the insufflator (1) and connected to the gas recirculation circuit in an area between the return duct (9) and the heater (4), said electronic safety valve (15) having an outlet to the outside of the insufflator (1).

Figure 2:
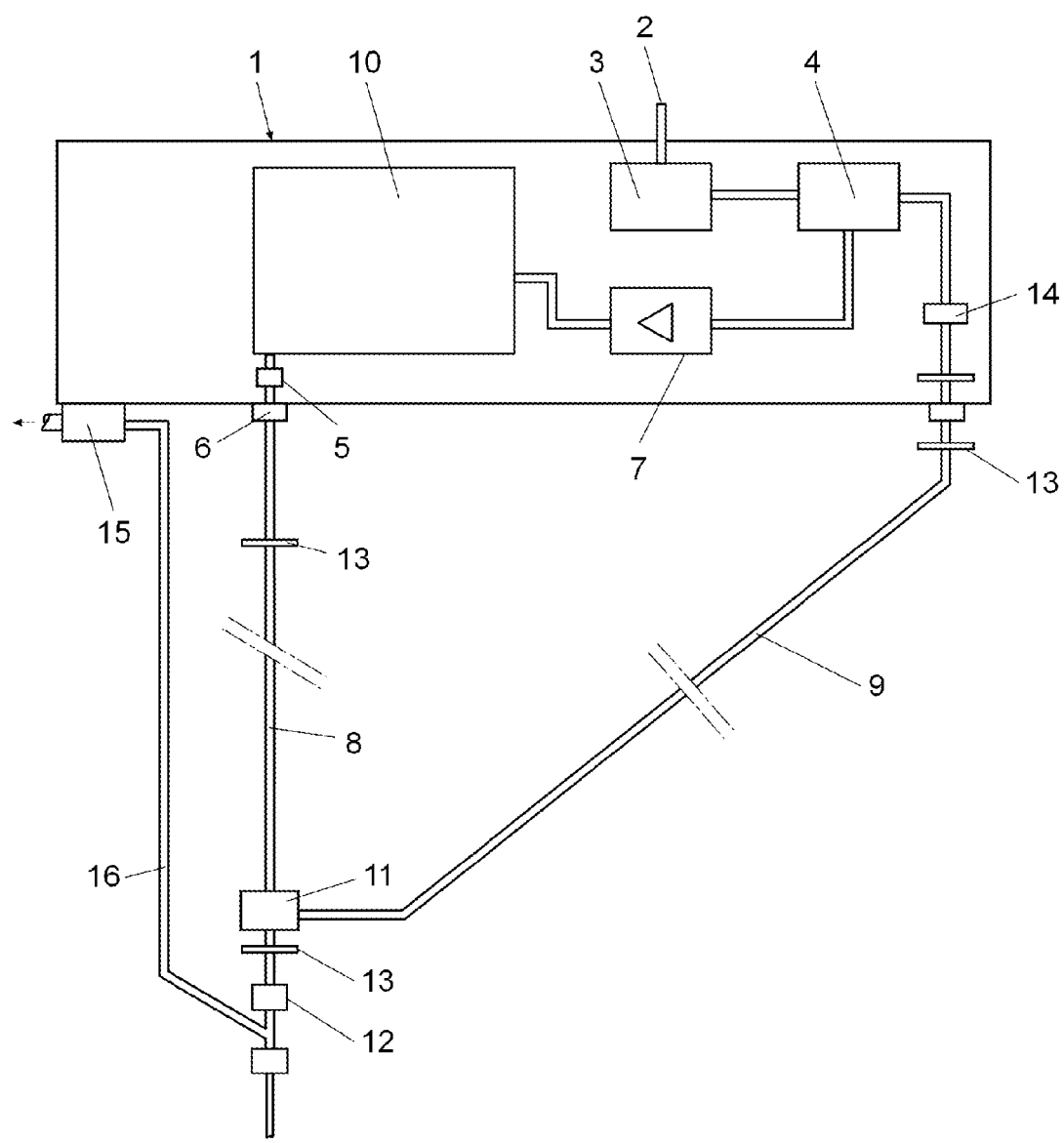
FIG. 2 shows a schematic view of an alternative embodiment of the system according to the invention, wherein the electronic safety valve against overpressures is arranged outside the insufflator and connected to the gas recirculation circuit by means of a bypass duct.

In the embodiment variant shown in FIG. 2, said electronic safety valve (15) is advantageously arranged outside the insufflator (1) and connected to the distal area of the gas supply duct (8) by means of a bypass duct (16). This external arrangement of the electronic safety valve (15) further reduces the risk of contamination of the insufflator.

Once the nature of the invention as well as an example of preferred embodiment have been sufficiently described, it is stated for all pertinent purposes, that the materials, form, size and arrangement of the elements described are susceptible to changes, provided these do not involve an alteration of the essential characteristics of the invention that are claimed subsequently.

The invention claimed is:

1. A system for heated gas insufflation in patients, comprising:
   an insufflator (1) provided with: a gas inlet (2), a valve (3) that regulates the flow of gas to be supplied, an adjustable heater (4) for the gas to be supplied, a sensor (5) that detects the temperature of the heated gas, an outlet (6) for supplying the gas, and means (7) for propelling the gas toward the supply outlet (6); and
   a disposable supply duct (8), that may be coupled to the gas outlet (6) of the insufflator in order to convey the gas, heated and supplied by the insufflator (1), into a patient's cavity, wherein the system comprises a gas return duct (9) connected to the supply duct (8) at an area near an end intended to be introduced into a patient's cavity and to an inlet of the heater (4), the gas supply duct (8) and the gas return duct (9) forming a continuous recirculation circuit for the gas that is heated at a constant supply temperature, said gas being recirculated inside said continuous recirculation circuit without entering said cavity and the gas insufflated into said cavity leaving said recirculation circuit and not being recirculated into said recirculation circuit.

2. The system according to claim 1, further comprising, between the heater (4) and the supply duct (8), a storage reservoir (10) through which the gas heated in the insufflator (1) circulates.

3. The system according to claim 1, wherein the supply duct (8) has a temperature sensor (11) at a distal area near the end intended to be introduced into the patient's cavity.

4. The system according claim 1, wherein, at least in the return duct (9), the recirculation circuit for the heated gas has a filter (13) for cleaning the circulating gas.

5. The system according to claim 1, wherein the recirculation circuit for the heated gas has an exhaust valve (12) through which controlled exhaust of the heated gas is adjusted.

6. The system according to claim 1, wherein the recirculation circuit for the heated gas comprises a mechanical safety valve (14) arranged inside the insufflator (1).

7. The system according to claim 1, further comprising an electronic safety valve (15) for releasing gas overpressures in the recirculation circuit to the outside.

8. The system according to claim 7, wherein the electronic safety valve (15) is arranged inside the insufflator (1) and connected to the gas recirculation circuit in an area between the return duct (9) and the heater (4), said safety electronic valve (15) having an outlet to the outside of the insufflator (1).

9. The system according to claim 7, wherein the electronic safety valve (15) is arranged outside the insufflator (1) and connected to the distal area of the gas supply duct (8) by means of a bypass duct (16).

* * * * *